(12) United States Patent
Ren et al.

(10) Patent No.: US 12,286,389 B2
(45) Date of Patent: Apr. 29, 2025

(54) CRYSTALLINE FORM A OF 2, 2-BIS(4-FLUOROPHENYL)-2-PHENYLACETAMIDE AND PREPARATION METHOD THEREFOR AND APPLICATION THEREOF

(71) Applicant: SHENZHEN RENTAI PHARMATECH LTD., Guangdong (CN)

(72) Inventors: Guobin Ren, Shenzhen (CN); Dongxu Yi, Shenzhen (CN); Weijie Ji, Shenzhen (CN); Jiajun Huang, Shenzhen (CN)

(73) Assignee: SHENZHEN JINGTAI TECHNOLOGY CO., LTD, Guangdong (CN)

( * ) Notice: Subject to any disclaimer, the term of this patent is extended or adjusted under 35 U.S.C. 154(b) by 811 days.

(21) Appl. No.: 17/487,047

(22) Filed: Sep. 28, 2021

(65) Prior Publication Data
US 2022/0033347 A1 Feb. 3, 2022

Related U.S. Application Data

(63) Continuation of application No. PCT/CN2019/080419, filed on Mar. 29, 2019.

(51) Int. Cl.
C07C 233/11 (2006.01)

(52) U.S. Cl.
CPC ........ C07C 233/11 (2013.01); *C07B 2200/13* (2013.01)

(58) Field of Classification Search
CPC .. C07C 233/11; C07B 2200/13; A61K 31/165
See application file for complete search history.

(56) References Cited

U.S. PATENT DOCUMENTS

| 6,288,122 | B1 | 9/2001 | McNaughton-Smith et al. |
| 2009/0036538 | A1* | 2/2009 | Castle ..................... A61P 11/00 514/617 |
| 2010/0056637 | A1 | 3/2010 | Castle et al. |
| 2018/0042872 | A1 | 2/2018 | Tubman |
| 2020/0197934 | A1 | 6/2020 | Amshey et al. |

FOREIGN PATENT DOCUMENTS

| CN | 1344158 A | 4/2002 |
| CN | 101437403 A | 5/2009 |
| WO | 2017070536 A1 | 4/2017 |

OTHER PUBLICATIONS

International Searching Authority (CN/ISA); International Search Report; Mail Date: Jul. 31, 2019; pp. 1-6.
International Searching Authority (CN/ISA); Written Opinion; Mail Date: Jul. 31, 2019; pp. 1-5.
International Searching Authority; Written Opinion of the ISA; Date: Jul. 31, 2019; pp. 1-7.
Intellectual Property of China; First Office Action of Corresponding CN application No. 201980003580 with Translation; Date: Mar. 17, 2021; pp. 1-6.

* cited by examiner

*Primary Examiner* — Deborah D Carr
(74) *Attorney, Agent, or Firm* — Taft Stettinius & Hollister LLP; Stephen F. Rost

(57) ABSTRACT

A crystalline form A of 2,2-bis(4-fluorophenyl)-2-phenylacetamide is provided. The crystalline form has good light stability, high temperature stability, and high humidity stability.

24 Claims, 12 Drawing Sheets

CRYSTALLINE FORM A OF 2, 2-BIS(4-FLUOROPHENYL)-2-PHENYLACETAMIDE AND PREPARATION METHOD THEREFOR AND APPLICATION THEREOF

RELATED APPLICATIONS

This application is a continuation application of International Patent Application No. PCT/CN2019/080419 with an international filing date of Mar. 29, 2019, designating the United States, the disclosure of which is hereby incorporated by reference in its entirety.

FIELD OF THE DISCLOSURE

The present application relates to the technical field of crystal form preparation, in particular to a crystal form A of 2,2-bis(4-fluorophenyl)-2-phenylacetamide, preparation method therefor and use thereof.

BACKGROUND 2,2-bis(4-fluorophenyl)-2-phenylacetamide of formula (I), also known as Senicapo, is an inhibitor of potassium flux developed by ICAGEN, INC. This compound is known as a drug for treating or preventing sickle cell disease, preventing erythrocyte dehydration and inhibiting potassium flux (CN 1344158B), and a drug for preventing or treating inflammatory processes or stroke (CN101437403B). Recent studies show that Senicapoc may be a potential drug for treating hereditary xerocytosis.

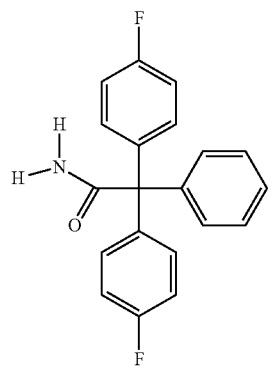

(I)

CN101437403B discloses a preparation method of the compound of formula (I). By referring to the following scheme, the preparation method comprises: (1) reacting phenylmagnesium bromide with difluorobenzophenone to prepare bis(4-fluorophenyl)phenylmethanol; (2) reacting bis(4-fluorophenyl)phenylmethanol with acetyl chloride to prepare bis(4-fluorophenyl)phenylchloromethane (3) reacting bis(4-fluorophenyl)phenylchloromethane with copper cyanide, followed by separating and purifying a residue by high performance liquid chromatography (HPLC) to prepare the compound of formula (I).

The inventors of the present application prepared the compound of formula (I) according to the preparation method as described in CN101437403B, and carried out analysis. The results showed that the prepared compound of formula (I) would undergo crystal transition in environment of high temperature or high humidity or under lights, and the resulting compound is unstable in physical state, thus cannot be used as a bulk pharmaceutical chemical. Therefore, a strict management would be required during use of the compound, rendering the compound unsuitable for use as a bulk pharmaceutical chemical.

SUMMARY

Accordingly, it is an object of the present application to provide a crystal form A of 2, 2-bis(4-fluorophenyl)-2-phenylacetamide of formula (I), a preparation method therefor and use thereof. The crystal A has significantly improved stability and has a residual solvent content significantly reduced to below 0.03%.

In one aspect, the present application provides a crystal form A of 2,2-bis(4-fluorophenyl)-2-phenylacetamide, wherein the X-ray powder diffraction thereof using Cu-Kα radiation has characteristic peaks at 2θ diffraction angles of 10.4±0.2°, 11.8±0.2°, 18.8±0.2° and 21.3±0.2°.

In some embodiments, the X-ray powder diffraction thereof using Cu-Kα radiation has further characteristic peaks at 2θ diffraction angles of 7.2±0.2°, and 20.8±0.2°.

In some embodiments, the X-ray powder diffraction thereof using Cu-Kα radiation has further characteristic peaks at 2θ diffraction angles of 15.2±0.2°, 23.0±0.2°, and 25.7±0.2°.

In some embodiments, the X-ray powder diffraction thereof using Cu-Kα radiation has further characteristic peaks at 2θ diffraction angles of 13.4±0.2°, 14.3±0.2°, 16.4±0.2°, 19.2±0.2°, 19.8±0.2°, 20.3±0.2°, and 24.1±0.2°.

In some embodiments, the X-ray powder diffraction thereof using Cu-Kα radiation has further characteristic peaks at 2θ diffraction angles of 22.1±0.2°, 22.5±0.2°, 25.0±0.2°, 26.5±0.2°, 27.5±0.2°, 28.5±0.2°, 29.5±0.2°, 31.6±0.2°, and 32.6±0.2°.

In some embodiments, the crystal form A has following characteristic peaks in X-ray powder diffraction pattern:

| No. of Peaks | 2θ (°) | I % |
| --- | --- | --- |
| 1 | 10.44 | 48.4 |
| 2 | 11.779 | 48.1 |
| 3 | 13.381 | 24 |
| 4 | 14.299 | 32.1 |
| 5 | 15.22 | 38.1 |
| 6 | 18.76 | 100 |
| 7 | 19.24 | 47 |
| 8 | 19.78 | 57.3 |
| 9 | 20.28 | 52 |
| 10 | 20.84 | 69.3 |
| 11 | 21.339 | 80.1 |
| 12 | 22.96 | 40.4 |
| 13 | 24.08 | 32.7 |
| 14 | 25.699 | 48.5 |

In some embodiments, the crystal form A has following characteristic peaks in X-ray powder diffraction pattern:

| No. of Peaks | 2-Theta | I % |
| --- | --- | --- |
| 1 | 7.163 | 6.4 |
| 2 | 10.44 | 48.4 |
| 3 | 11.779 | 48.1 |
| 4 | 13.381 | 24 |
| 5 | 14.299 | 32.1 |
| 6 | 15.22 | 38.1 |
| 7 | 16.401 | 7.4 |
| 8 | 18.76 | 100 |

-continued

| No. of Peaks | 2-Theta | I % |
|---|---|---|
| 9 | 19.24 | 47 |
| 10 | 19.78 | 57.3 |
| 11 | 20.28 | 52 |
| 12 | 20.84 | 69.3 |
| 13 | 21.339 | 80.1 |
| 14 | 22.96 | 40.4 |
| 15 | 24.08 | 32.7 |
| 16 | 24.962 | 12 |
| 17 | 25.699 | 48.5 |
| 18 | 26.5 | 11.1 |
| 19 | 27.54 | 8.4 |
| 20 | 28.46 | 25.9 |
| 21 | 29.517 | 15.8 |
| 22 | 31.58 | 36 |
| 23 | 32.599 | 18 |

In some embodiments, the crystal form A has an X-ray powder refraction pattern substantially as shown in FIG. 4.

In some embodiments, the crystal form A has a characteristic endothermic peak in a temperature range of 177.0° C.-191.0° C. measured by differential scanning calorimetry.

In some embodiments, the crystal form A has a differential scanning calorimetry curve substantially as shown in FIG. 5.

In some embodiments, the crystal form A has a weight loss of 0.02584% before a temperature of 100° C. in its thermo gravimetric analysis curve.

In some embodiments, the crystal form A has a thermo gravimetric analysis curve substantially as shown in FIG. 6.

In another aspect, the present application also provides a method for preparing the crystal form A, comprising the following steps of: dissolving 2,2-bis(4-fluorophenyl)-2-phenylacetamide by adding a good solvent thereto, evaporating the solvent or cooling to give a solid, and drying the solid to obtain the crystal form A.

In some embodiments, said dissolving is performed by adding the good solvent at a temperature of 50° C. to 75° C., and said cooling is performed at a temperature of 18° C. to 5° C.' to give a solid.

In another aspect, the present application further provides a method for preparing the crystal form A, comprising the following steps of: dissolving 2,2-bis(4-fluorophenyl)-2-phenylacetamide by adding a good solvent thereto, then adding a poor solvent to obtain a solid, and drying the solid to obtain the crystal form A.

In some embodiments, said dissolving is performed by adding the good solvent at a temperature of 15° C. to 35° C., and said adding a poor solvent is performed at a temperature of 15° C. to 35° C. to obtain a solid.

In some embodiments, the good solvent is an organic solvent selected from the group consisting of a lower alcohol, a lower ketone, a lower ester, a lower nitrile, and a lower ether; preferably, the lower alcohol is selected from the group consisting of methanol, ethanol, isopropanol or n-butanol, the lower ketone is acetone, the lower ester is ethyl acetate, the lower ether is tetrahydrofuran or dioxane, and the lower nitrile is acetonitrile.

In some embodiments, a ratio of 2,2-bis(4-fluorophenyl)-2-phenylacetamide to the good solvent is (10-40) mg: (0.1-5) mL.

In some embodiments, the poor solvent is select from n-heptane, n-hexane, absolute ethyl ether, isopropyl ether or water.

In another aspect, the present application further provides a pharmaceutical composition, comprising the crystal form A and a pharmaceutically acceptable excipient.

In another aspect, the present application further provides use of a pharmaceutically effective amount of the crystal form A, or of the crystal form A prepared by the method, or of the pharmaceutical composition, in the manufacture of a medicament for preventing or treating an inflammatory process or stroke.

In some embodiments, the inflammatory process is select from the group consisting of multiple sclerosis, insulin-dependent diabetes mellitus, rheumatoid arthritis, peripheral neuritis, and pulmonary hypertension.

In another aspect, the present application further provides use of a pharmaceutically effective amount of the crystal form A, or of the crystal form A prepared by the method, or of the pharmaceutical composition, for inhibition of cell potassium channel, reduction of erythrocyte dehydration, treatment or prevention of sickle cell disease, or enhancement of the resistance to degradation of a phenyl-containing potassium channel inhibitor in a biological medium.

In some embodiments, the medicament is administered orally, parenterally, intradermally, intrathecally, intramuscularly, subcutaneously, vaginally, as a buccal, sublingually, rectally, as a topical, inhalation, intranasal, or transdermally.

In another aspect, the present application further provides a method for the inhibition of cell potassium channel, reduction of erythrocyte dehydration, treatment or prevention of sickle cell disease, enhancement of the resistance to degradation of a phenyl-containing potassium channel inhibitor in a biological medium, preventing or treating an inflammatory process or stroke, comprising the step of administering a pharmaceutically effective amount of the pharmaceutical composition to a patient.

The technical solutions of the present application have the following advantages:

1. The crystal form A of the compound of formula (I) provided in the present application has high purity, and good solubility in water, buffer solution or organic solvent, which is beneficial to prepare a medicament.

2. The crystal form A of the compound of formula (I) provided in the present application has good light stability, high temperature stability, and high humidity stability, and has a moisture content or other solvent content as low as 0.03% (by mass). When the relative humidity is increased from 0 to RH 90%, the crystal form A show a weight increase by hygroscopicity of not higher than 1%, indicating the moisture absorption by the crystal form A is slow. The crystal form A can be prepared with a simple preparation process under mild conditions, and the quality is stable, all of which facilitate large-scale industrial production.

3. The crystal form A of the compound of formula (I) provided by the present application has an improved powder flowability when compared with crystal form I, and is suitable to prepare formulations with stable active ingredient content.

4. The crystal form A of the compound of formula (I) provided by the present application has better efficacy in animal body, longer half-life period and higher exposure when compared with crystal form I.

BRIEF DESCRIPTION OF THE DRAWINGS

In order to more clearly describe the specific embodiments of the present application or the technical solutions in the prior art, drawings used in the specific embodiments or the description of the prior art will be briefly introduced as follows. Obviously, the drawings in the following description are some embodiments of the present application, and other drawings can be obtained according to these drawings without paying creative labor for those skilled in the art.

Corresponding reference numerals are used to indicate corresponding parts in the drawings.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The term "bulk pharmaceutical chemical" used in the following Examples of the present application refers to 2,2-bis(4-fluorophenyl)-2-phenylacetamide, with a chemical purity of greater than 98%, provided by Shanghai Haoyuan Biomedical Technology Co., Ltd.

Following experimental equipment and test conditions are used in the present application:
X-Ray Powder Diffractometer XRPD
Model: Uitima IV (Rigaku, Japan)
Method: Cu target Ka, voltage: 40 KV, current: 40 mA, test angle: 3-45°, scanning step: 0.02, exposure time: 0.2 S, slit width of light pipe: 2 mm, Dtex detector.
X-Ray Single Crystal Diffractometer SXRD
Model: BRUKER D8 QUEST (BRUKER, Germany)
Method: Cu target, voltage: 40 KV, current: 30 mA
Differential Scanning Calorimeter DSC
Model: TA 2000 (TA Instruments, US)
Method: heating at a rate of 10° C./min.
Thermal Gravimetric Analysis TGA
Model: TA 500 (TA Instruments, US);
Method: heating at a rate of 10° C./min.
Dynamic Vapor Sorption DVS
Model: DVS intrinsic (SMS, British);
Method: 25° C., relative humidity is stepped up at a rate of 10%, the judgment standard is change in moisture content is <0.02% over a 10-minute period.
Light Incubator
Model: TES-1330A (TES Electronic Corp.)
ULTRASOUND Equipment
Model: KQ-3200 (Shanghai Alloy Ultrasonic Equipment Co., Ltd.)
Programmable Temperature and Humidity Chamber for Drug Stability
Model: CMA-100C (Shanghai Puhan Precision Equipment Co., Ltd.)

Example 1 XRPD Analysis of Bulk Pharmaceutical Chemical 2,2-bis(4-fluorophenyl)-2-phenylacetamide, with a chemical purity of greater than 98%, purchased from and prepared by Shanghai Haoyuan Biomedical Technology Co., Ltd. according to the method disclosed in CN101437403B, is used as bulk pharmaceutical chemical.

Figure 1:
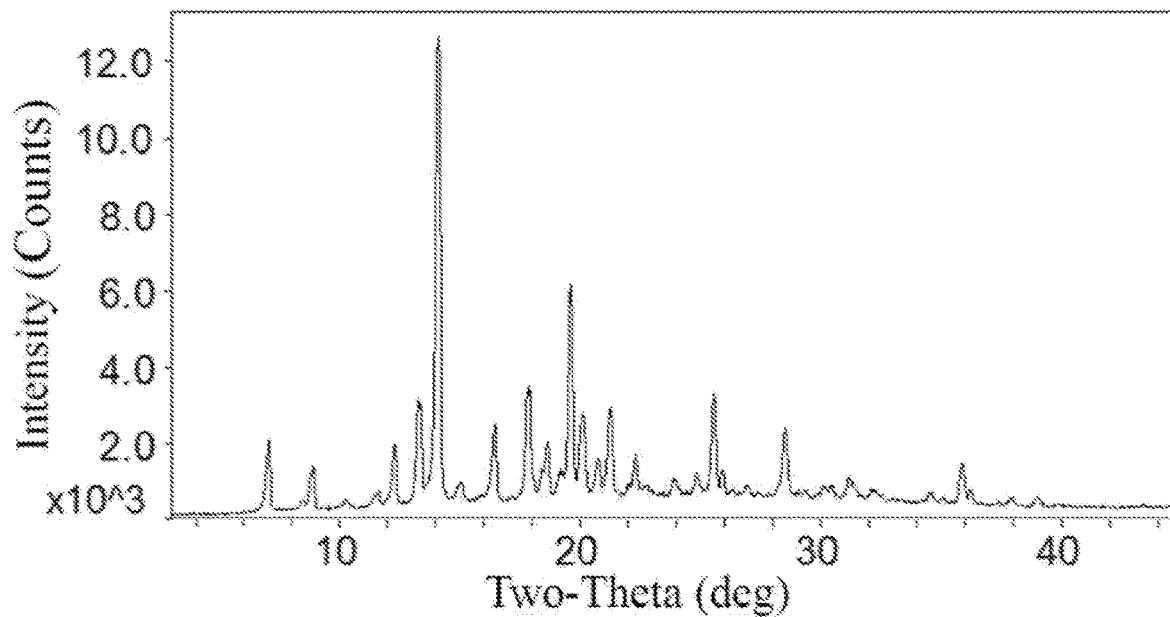
FIG. 1 shows an X-ray powder diffraction (XRPD) pattern of crystal form I in Example 1 of the present application.

XRPD pattern for the bulk pharmaceutical chemical is measured and shown in FIG. 1. The characteristic peaks are listed in the below table. It is confirmed that the compound prepared by the method disclosed in CN101437403B is a crystal, marked as crystal form I.

TABLE 1

| Characteristic peaks of crystal form I | | |
|---|---|---|
| 2-Theta | d (A) | I % |
| 7.04 | 12.5464 | 15 |
| 12.28 | 7.2019 | 11.5 |
| 13.281 | 6.6612 | 25.2 |
| 14.1 | 6.2759 | 100 |
| 16.459 | 5.3814 | 16.8 |
| 17.879 | 4.9572 | 27.7 |
| 18.639 | 4.7566 | 10.8 |

TABLE 1-continued

Characteristic peaks of crystal form I

| 2-Theta | d (A) | I % |
|---|---|---|
| 19.582 | 4.5297 | 49.6 |
| 20.12 | 4.4096 | 16.3 |
| 21.259 | 4.1758 | 18.8 |
| 22.301 | 3.9831 | 10.8 |
| 25.541 | 3.4847 | 22.9 |
| 28.501 | 3.1292 | 17.7 |

Figure 2:
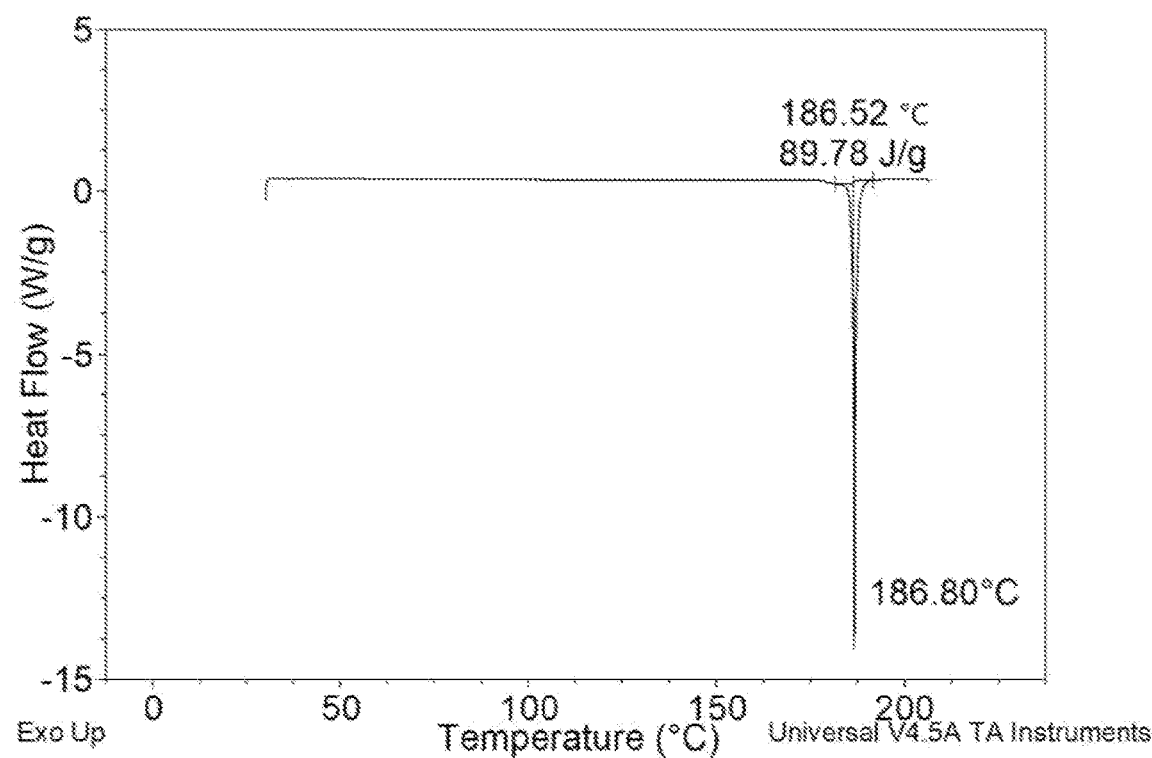
FIG. 2 shows a differential scanning calorimetry (DSC) curve of crystal form I in Example 1 of the present application.
Figure 3:
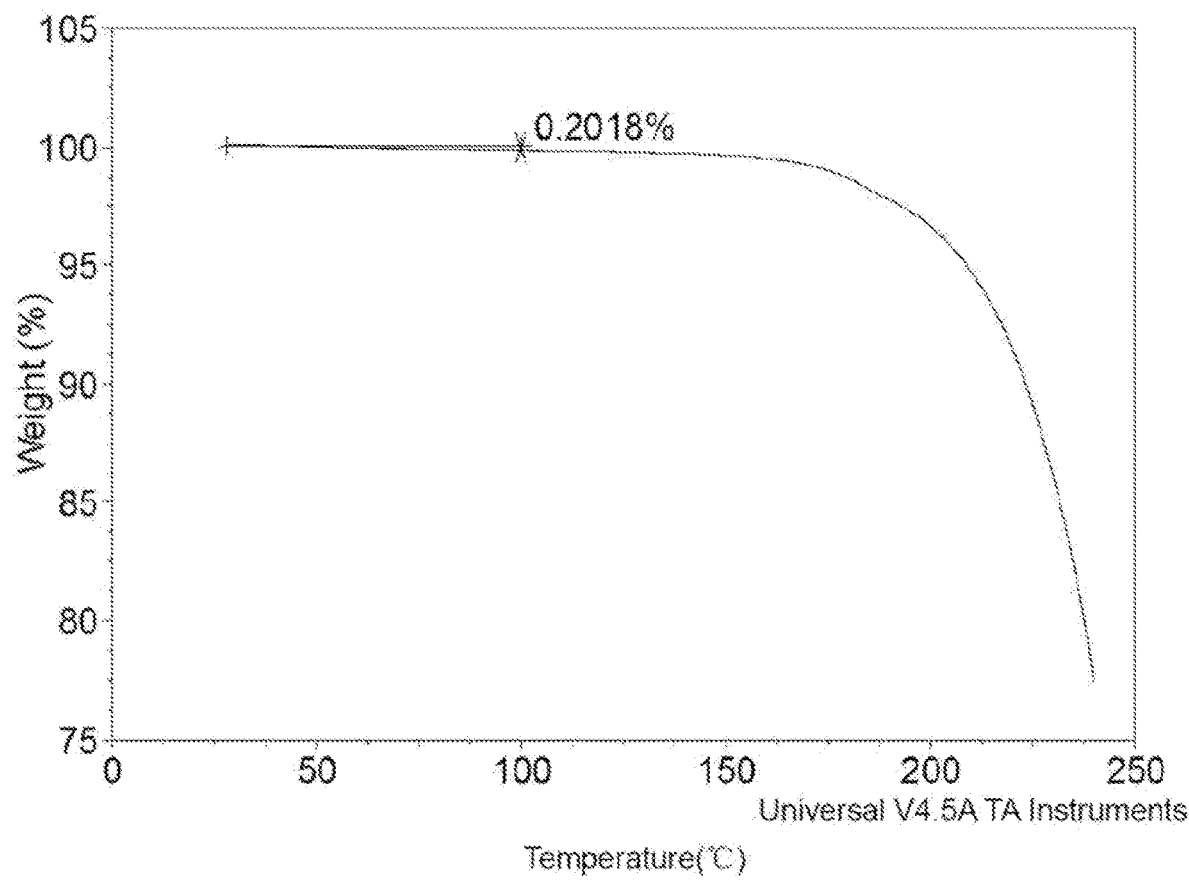
FIG. 3 shows a thermo gravimetric analysis (TGA) curve of crystal form I in Example 1 of the present application.

DSC and TGA curves for the bulk pharmaceutical chemical are measured and shown in FIGS. 2 and 3. It is observed that, the crystal form I has one characteristic endothermic peak at 184.0-191.0° C. in the DSC curve, and a weight loss of 0.2018% before 100° C. in the TGA curve.

Example 2 Preparation of Crystal Form A 16 mg of the bulk pharmaceutical chemical is weighed out and placed into a sample bottle, and 0.6 mL of absolute ethyl alcohol is added thereto for dissolving at room temperature to obtain a clear solution. The clear solution is allowed to undergo slow evaporation to give an orange solid which is then vacuum dried at room temperature to give a crystal form A as an orange powder. XRPD pattern of the crystal form A is measured and shown in FIG. 4. Characteristic peaks are listed in the table below.

TABLE 2

Characteristic peaks of crystal form A

| 2-Theta | d (A) | I % |
|---|---|---|
| 7.163 | 12.3313 | 6.4 |
| 10.44 | 8.4667 | 48.4 |
| 11.779 | 7.5069 | 48.1 |
| 13.381 | 6.6114 | 24 |
| 14.299 | 6.1893 | 32.1 |
| 15.22 | 5.8164 | 38.1 |
| 16.401 | 5.4001 | 7.4 |
| 18.76 | 4.7263 | 100 |
| 19.24 | 4.6092 | 47 |
| 19.78 | 4.4848 | 57.3 |
| 20.28 | 4.3753 | 52 |
| 20.84 | 4.2589 | 69.3 |
| 21.339 | 4.1604 | 80.1 |
| 22.14 | 4.0117 | 21 |
| 22.521 | 3.9447 | 44 |
| 22.96 | 3.8702 | 40.4 |
| 24.08 | 3.6928 | 32.7 |
| 24.962 | 3.5642 | 12 |
| 25.699 | 3.4636 | 48.5 |
| 26.001 | 3.424 | 20.4 |
| 26.5 | 3.3608 | 11.1 |
| 27.54 | 3.2361 | 8.4 |
| 28.46 | 3.1335 | 25.9 |
| 28.898 | 3.087 | 18.2 |
| 29.517 | 3.0237 | 15.8 |
| 30.219 | 2.9551 | 13.5 |
| 30.599 | 2.9192 | 13.9 |
| 31.58 | 2.8308 | 36 |
| 32.599 | 2.7445 | 18 |
| 34.761 | 2.5786 | 20.9 |
| 35.1 | 2.5545 | 20.9 |
| 36.002 | 2.4925 | 12 |
| 36.399 | 2.4662 | 10 |
| 38.158 | 2.3565 | 6.7 |
| 39.26 | 2.2929 | 7.7 |

Figure 5:
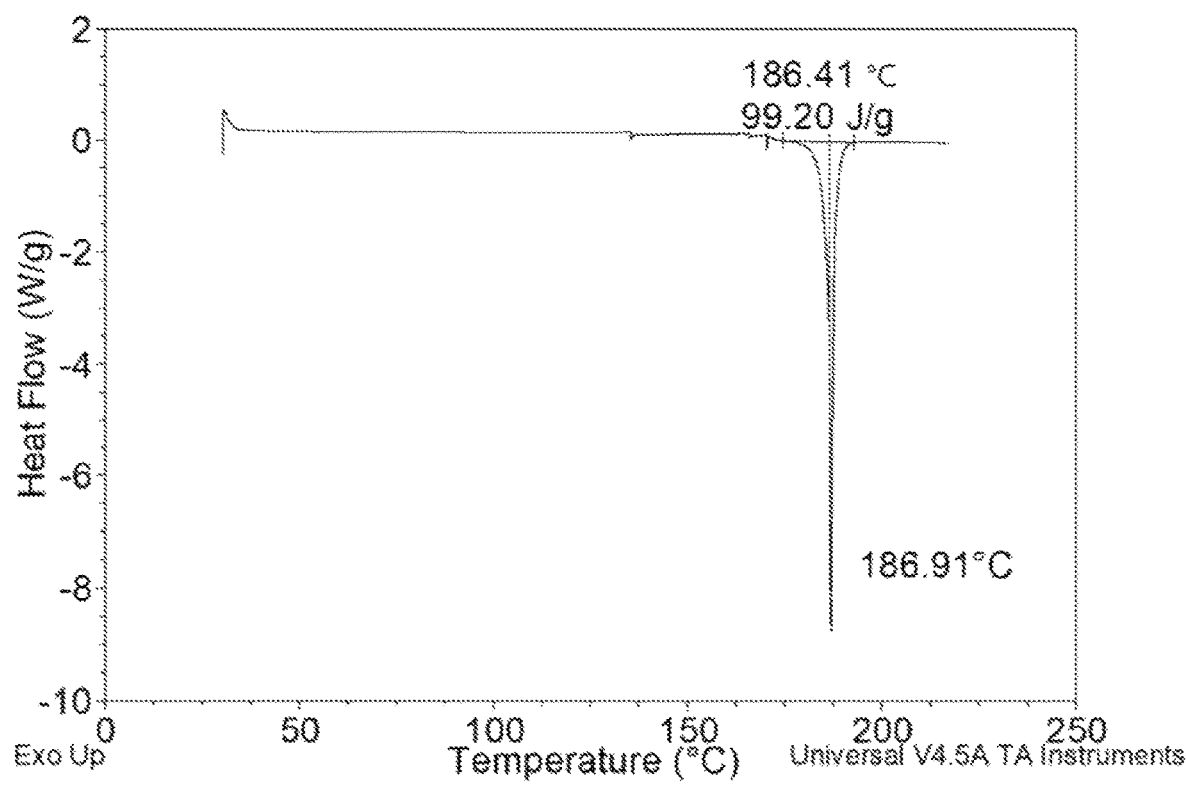
FIG. 5 shows a DSC curve of crystal form A in Example 2 of the present application.
Figure 6:
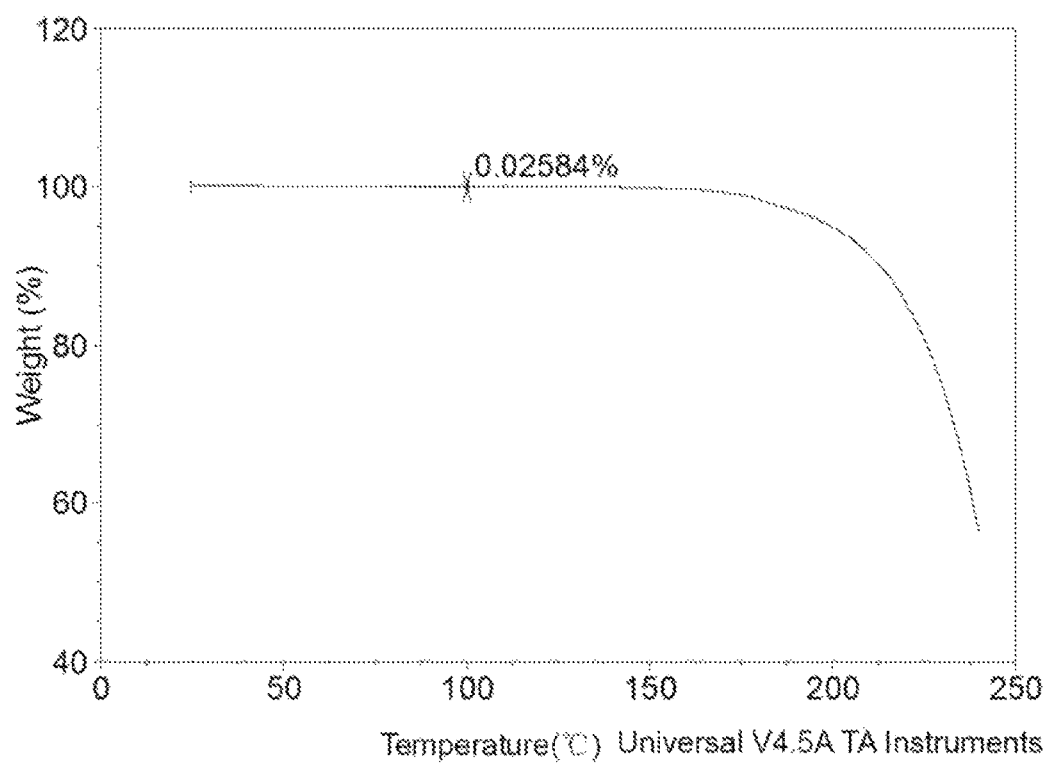
FIG. 6 shows a TGA curve of crystal form A in Example 2 of the present application.

DSC and TGA curves for the orange powder are measured and shown in FIGS. 5 and 6. It is observed that, the crystal form A has one characteristic endothermic peak at 179.0-191.0° C. in the DSC curve, and a weight loss of 0.02584% before 100° C. in the TGA curve. The crystal form A melts and decomposes, indicating it is a non-solvate.

Figure 7:
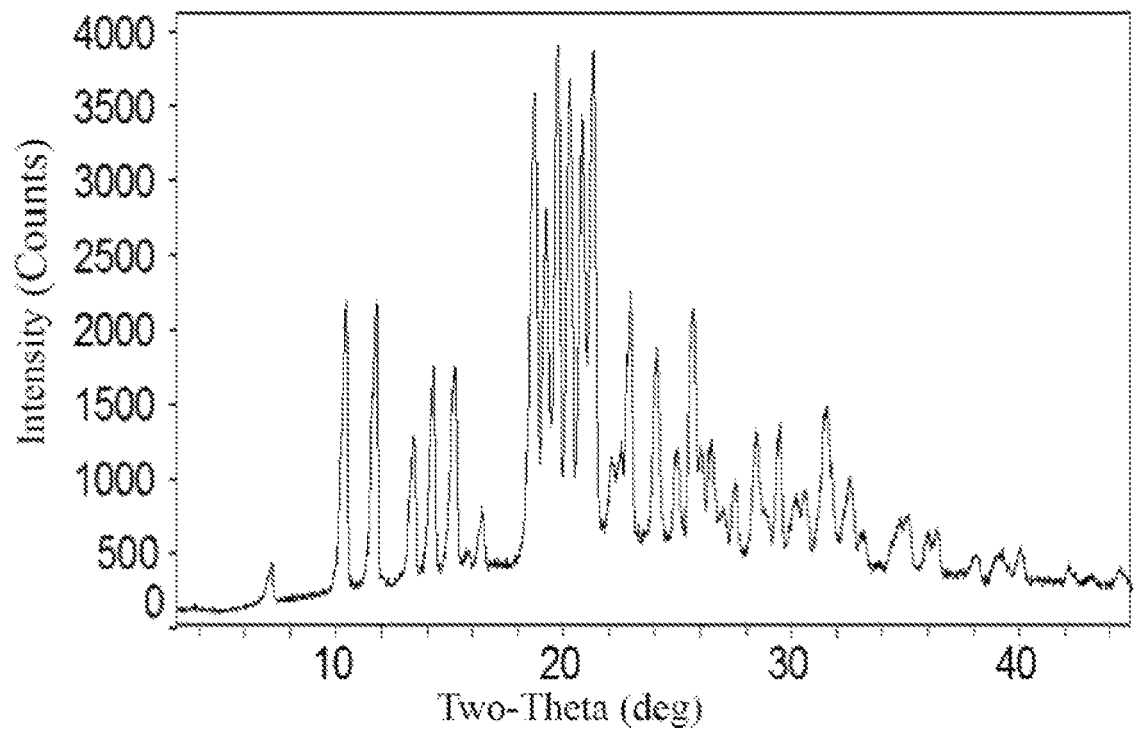
FIG. 7 shows an XRPD pattern of crystal form A in Example 3 of the present application.

Example 3 Preparation of Crystal Form A 15.1 mg of the bulk pharmaceutical chemical is weighed out and placed into a sample bottle, and 0.5 mL of ethyl acetate is added thereto for dissolving at room temperature to obtain a clear solution. The clear solution is allowed to undergo slow evaporation to give a pink solid which is then vacuum dried at room temperature to give a pink powder. XRPD pattern of the pink powder is measured and shown in FIG. 7 which is substantially consistent with FIG. 4 of Example 2.

Figure 8:
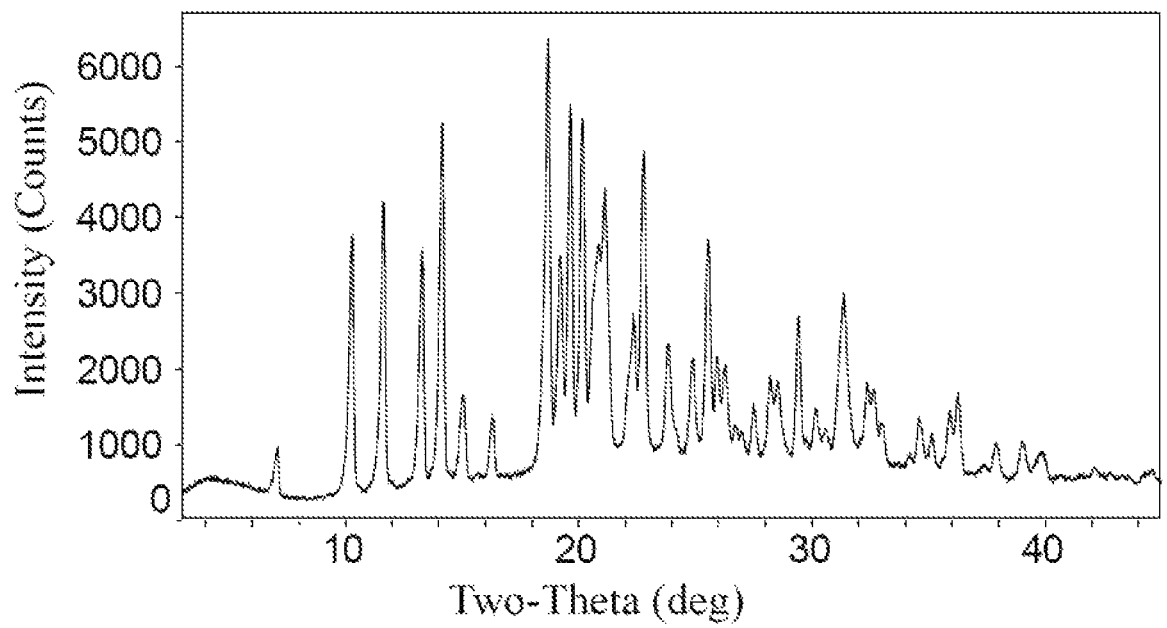
FIG. 8 shows an XRPD pattern of crystal form A in Example 4 of the present application.

Example 4 Preparation of Crystal Form A 15.2 mg of the bulk pharmaceutical chemical is weighed out and placed into a sample bottle, and 0.2 mL of 1,4-dioxane is added thereto for dissolving at room temperature to obtain a clear solution. The clear solution is allowed to undergo slow evaporation to give a white solid which is then vacuum dried at room temperature to give a white powder. XRPD pattern of the white powder is measured and shown in FIG. 8 which is substantially consistent with FIG. 4 of Example 2.

Figure 9:
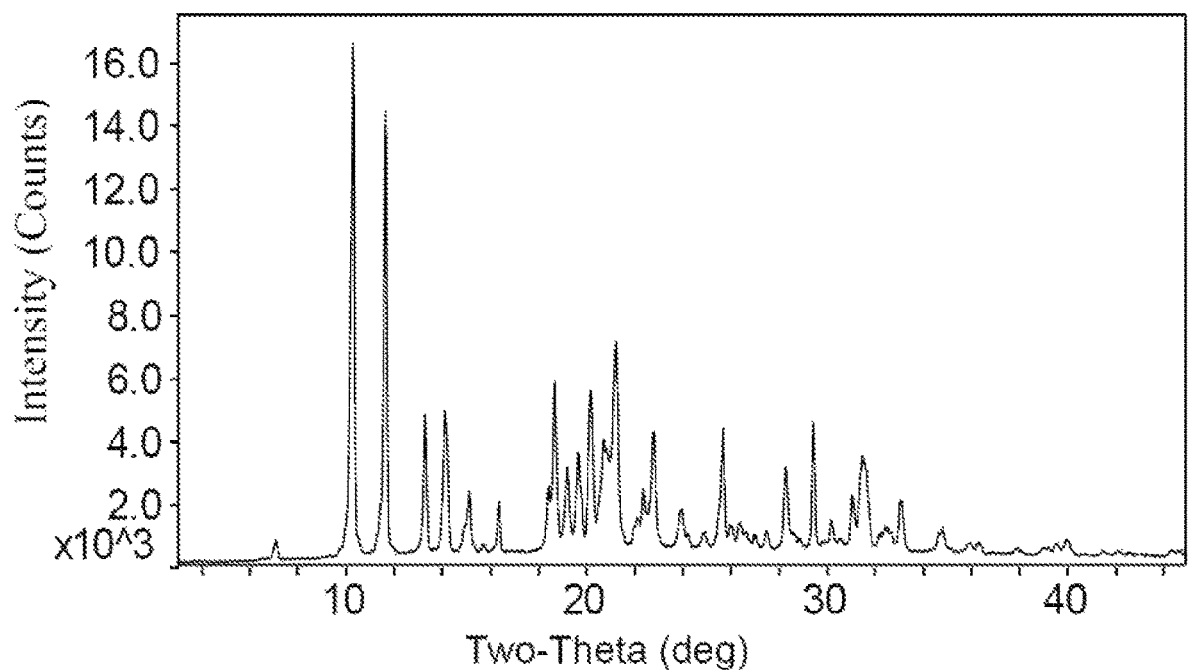
FIG. 9 shows an XRPD pattern of crystal form A in Example 5 of the present application.

Example 5 Preparation of Crystal Form A 38.0 mg of the bulk pharmaceutical chemical is weighed out and placed into a sample bottle, and 0.3 mL of acetonitrile is added thereto for dissolving at room temperature to obtain a clear solution. The clear solution is filtered by a filter head with a diameter of 0.45 μm to obtain a filtrate, then the filtrate is cooled at 4° C. to separate a white solid which is then filtered out and vacuum dried at room temperature to give a white solid. XRPD pattern of the white solid is measured and shown in FIG. 9 which is substantially consistent with FIG. 4 of Example 2.

Figure 10:
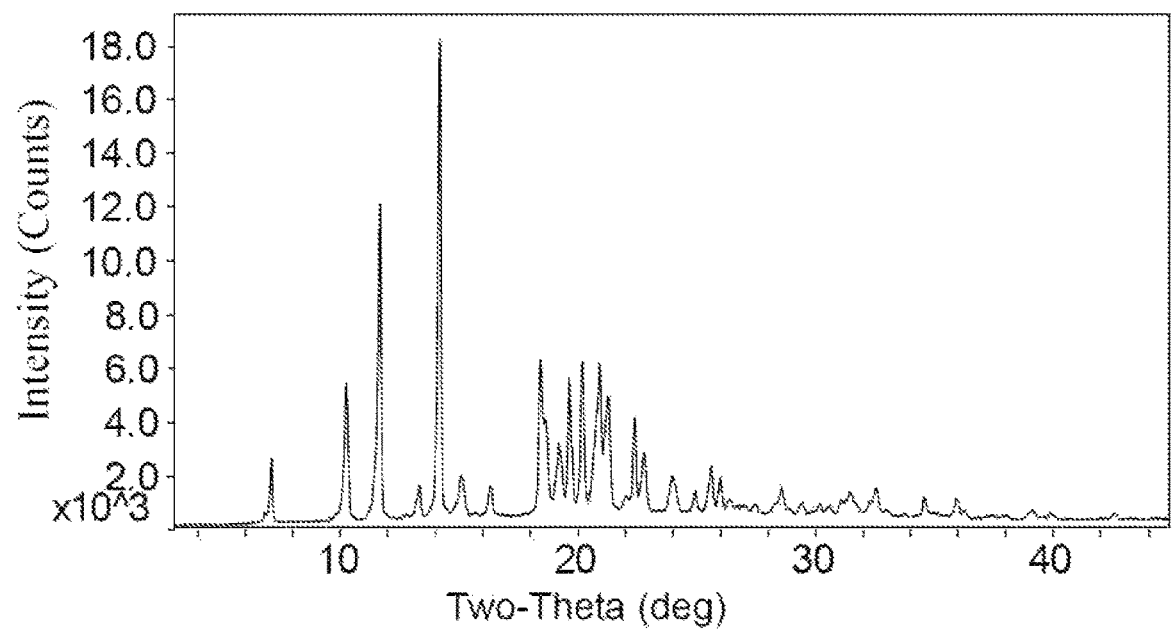
FIG. 10 shows an XRPD pattern of crystal form A in Example 6 of the present application.

Example 6 Preparation of Crystal Form A 35.0 mg of the bulk pharmaceutical chemical is weighed out and placed into a sample bottle, and 0.3 mL of acetone is added thereto and heated to 70° C. for dissolving to obtain a clear solution. The clear solution is filtered by a filter head with a diameter of 0.45 μm to obtain a filtrate, then the filtrate is cooled at 4° C. to separate a white solid which is then filtered out and vacuum dried at room temperature to give a white solid. XRPD pattern of the white solid is measured and shown in FIG. 10 which is substantially consistent with FIG. 4 of Example 2.

Figure 11:
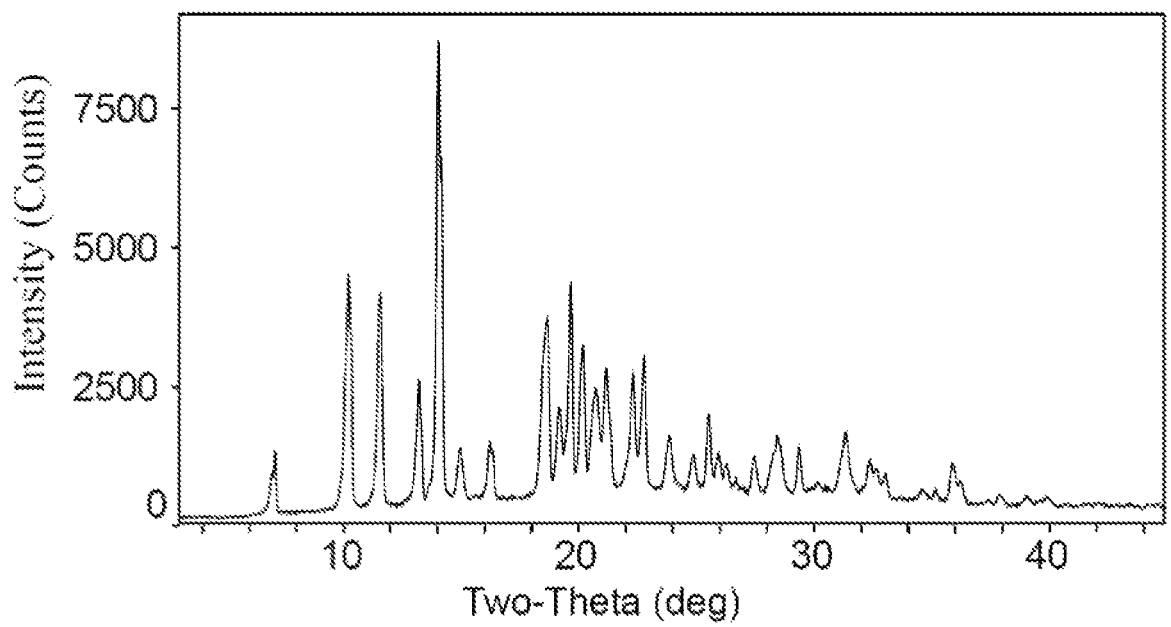
FIG. 11 shows an XRPD pattern of crystal form A in Example 7 of the present application.

Example 7 Preparation of Crystal Form A 14.2 mg of the bulk pharmaceutical chemical is weighed out and placed into a sample bottle, and 0.5 mL of tetrahydrofuran is added thereto, and 2 mL of n-heptane is slowly added dropwise thereto to obtain a pink turbid solution. The pink turbid solution is filtered to give a solid which is then vacuum dried at room temperature to give a pink solid. XRPD pattern of the pink solid is measured and shown in FIG. 11 which is substantially consistent with FIG. 4 of Example 2.

Figure 12:
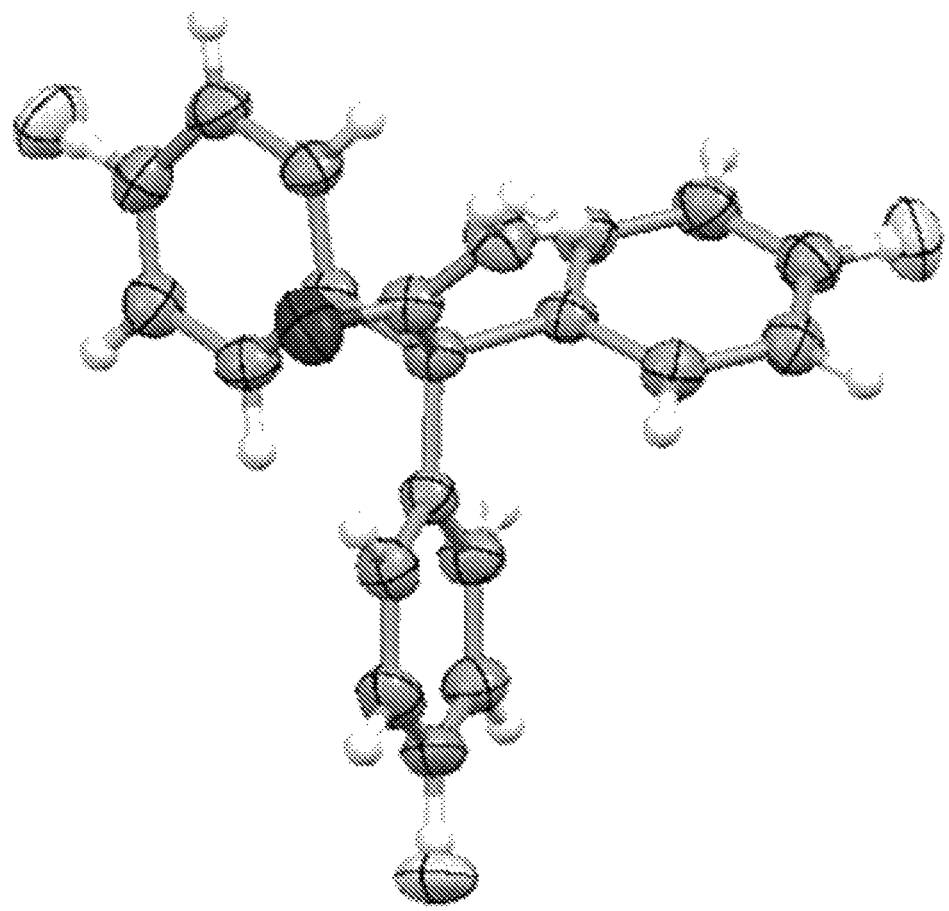
FIG. 12 shows a molecular ellipsoid diagram of single crystal structure of crystal form A in Example 8 of the present application.
Figure 13:
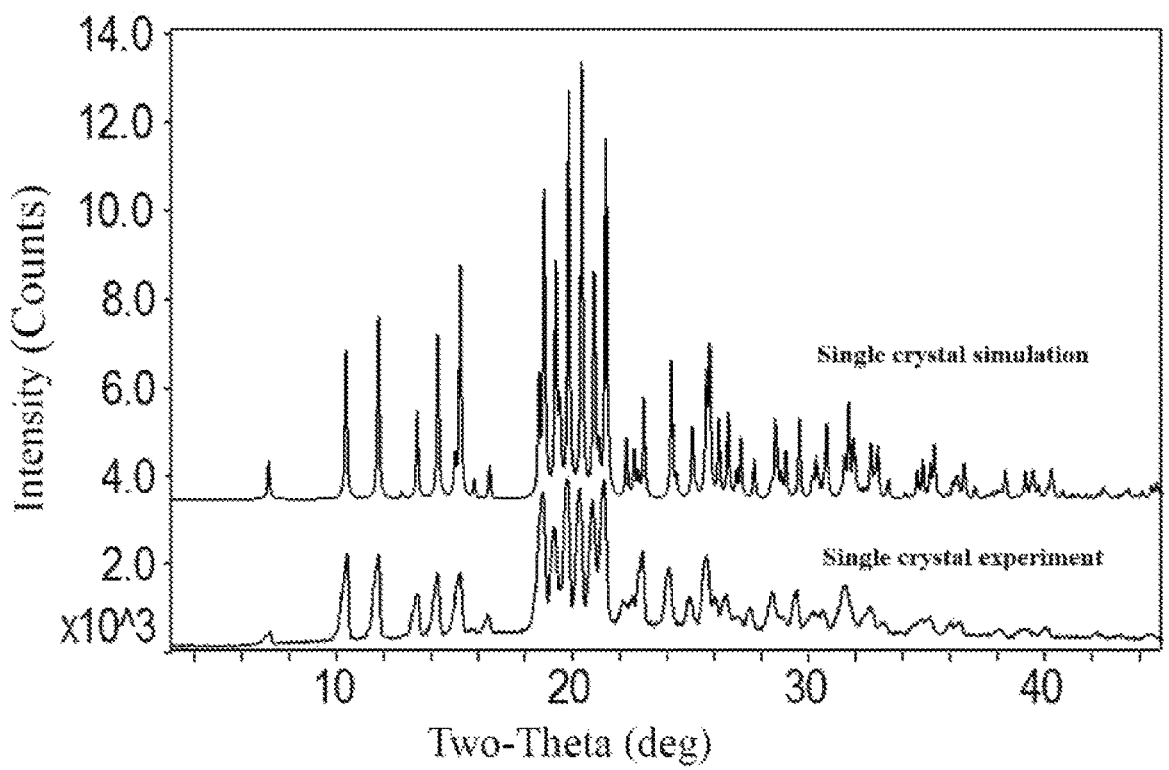
FIG. 13 shows comparison of XRPD patterns of digitally simulated single crystal structure to experimentally cultured single crystal structure, of crystal form A in Example 8 of the present application.

Example 8 Preparation of Single Crystal of Crystal Form A 15.9 mg of the bulk pharmaceutical chemical is weighed out and placed into a sample bottle, and 1.5 mL of absolute ethyl alcohol is added thereto for dissolving at room temperature to obtain a clear solution. The clear solution is allowed to undergo slow evaporation to give a single crystal of crystal form A. The obtained single crystal is analyzed with an X-ray single crystal diffractometer, and the obtained data is analyzed by crystallographic structural analysis, and the results are shown in table below. Molecular ellipsoid diagram of the single crystal structure is shown in FIG. 12. Comparison of XRPD patterns of digitally simulated single crystal structure to experimentally cultured single crystal structure of crystal form A is shown in FIG. 13.

TABLE 3

Data of single crystal

| | | |
|---|---|---|
| Identification code | Form A | |
| Empirical formula | $C_{25}H_{35}N_3O_2$ | |
| Formula weight | 409.56 | |
| Temperature | 273 (2) K | |
| Wavelength | 1.54178 Å | |
| Crystal system | Monoclinic | |
| Space group | $P2_1$ | |
| Unit cell dimensions | a = 9.523 (2) Å | □ = 90°. |
| | b = 9.923 (2) Å | □ = 101.829 (10)° |
| | c = 12.157 (2) Å | □ = 90°. |
| Volume | 1124.4 (4) Å$^3$ | |
| Z | 2 | |

Experimental Example 1 Yield and Purity Study

Purities of the crystal form I in Example 1 and the crystal forms A prepared in Examples 2-7 are determined by HPLC. The results are as shown in table 4.

TABLE 4

Experimental results of HPLC

| | Yield/% | Purity/% |
|---|---|---|
| Example 1 | 83.05 | 98.0 |
| Example 2 | 95.25 | 98.91 |
| Example 3 | 97.14 | 98.88 |
| Example 4 | 93.01 | 98.98 |
| Example 5 | 92.44 | 98.67 |
| Example 6 | 98.35 | 98.22 |
| Example 7 | 88.22 | 99.13 |

Data in the above table shows that, compared with crystal form I in Example 1, the crystal forms A prepared in Examples 2 to 7 of the present application have significantly improved purity.

Experimental Example 2 Hygroscopicity Study

Dynamic vapor sorption (DVS) experiment are performed for crystal form A in Example 2 to obtain DVS curves under the following conditions: the temperature is 25° C., the relative humidity (RH) is stepped up from RH 0 to RH 90% at a rate of RH 10% per step, with 10 min for each step to reach equilibrium.

Figure 14:
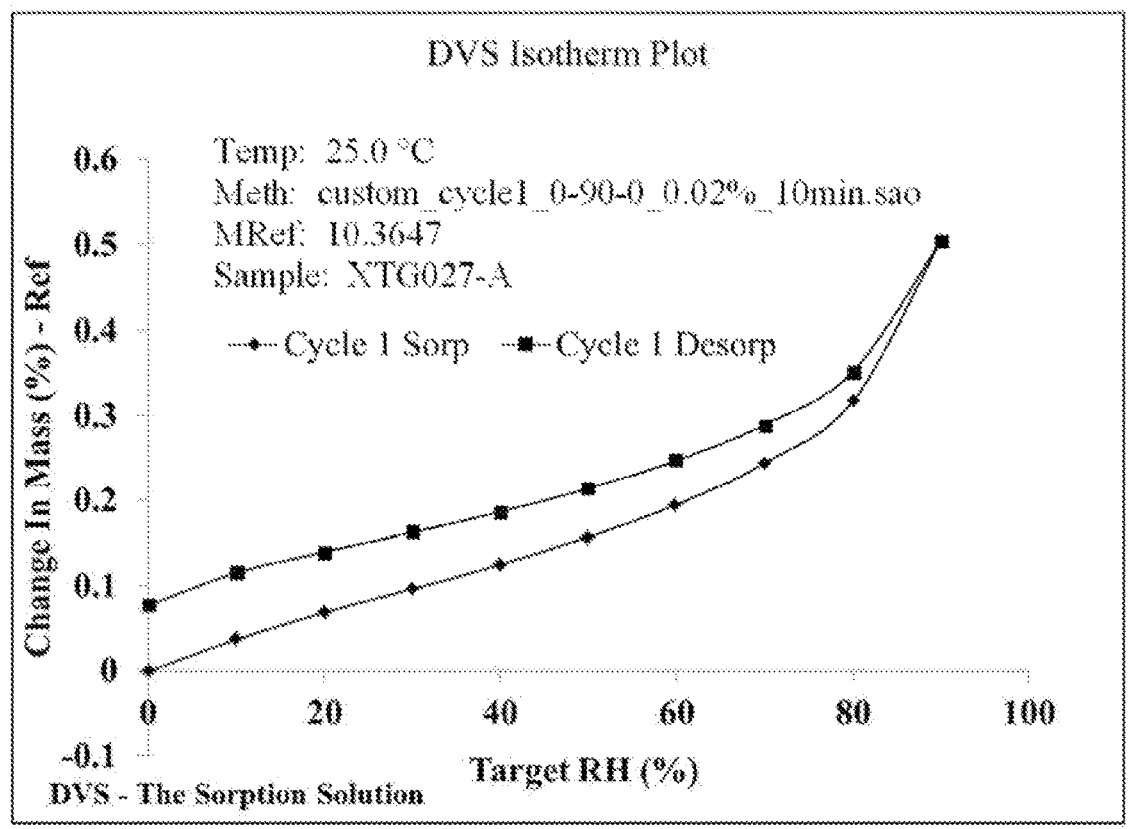
FIG. 14 shows a dynamic vapor sorption (DVS) curve of crystal form A in Example 2 of the present application.

When RH 90% is completed, the crystal form A has a weight increase of less than 0.6% due to moisture absorption, and in each step of 10 min, the crystal form A has a weight change of less than 0.02%, indicating that the crystal form A has a significantly reduced hygroscopicity, which is more conducive to transportation and storage of drugs (see FIG. 14).

Experimental Example 3 Stability Study of Crystal Form A

Figure 15:
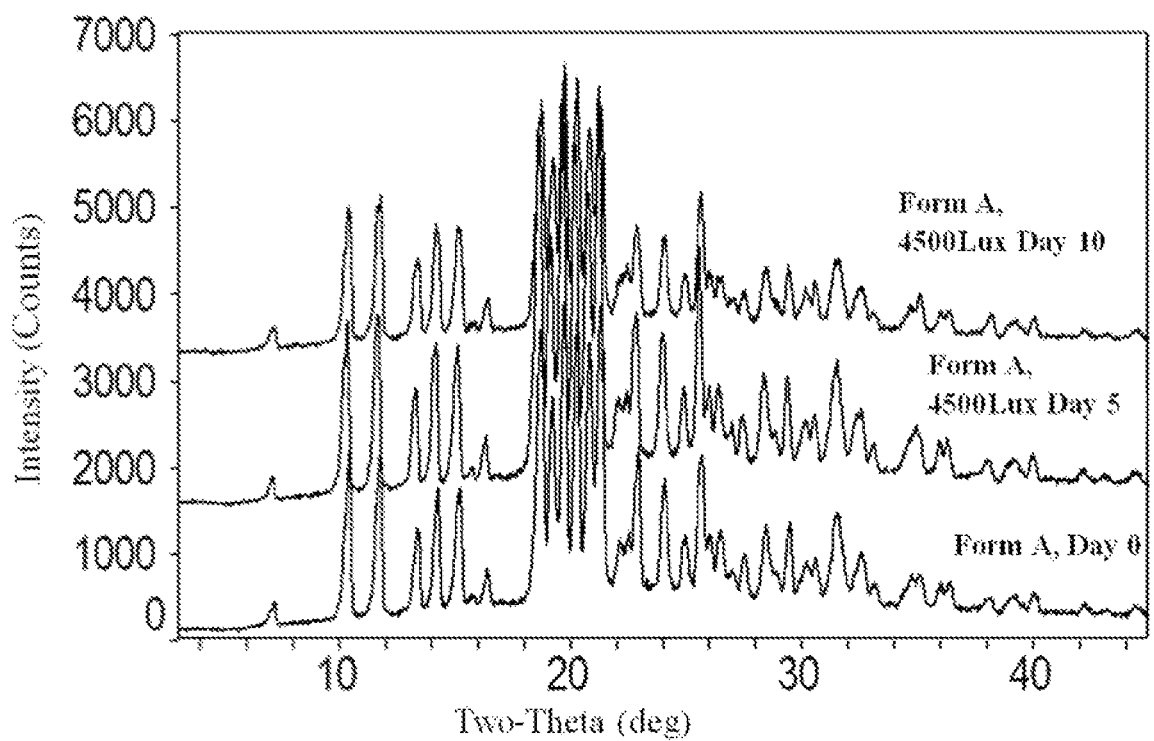
FIG. 15 shows comparison of XRPD patterns of crystal form A of the present application to study stability under lights.

Following tests are performed for the crystal form A prepared in Example 2:

(1) Light stability: the test sample is placed in an environment having a temperature of 25° C. and a light condition of 4500 Lux for 5 days and 10 days, respectively, to test the stability of the crystal form, which are compared with XRPD pattern of the crystal form A on day 0. The results are shown in FIG. 15, indicating that the crystal form A has good light stability.

Figure 16:
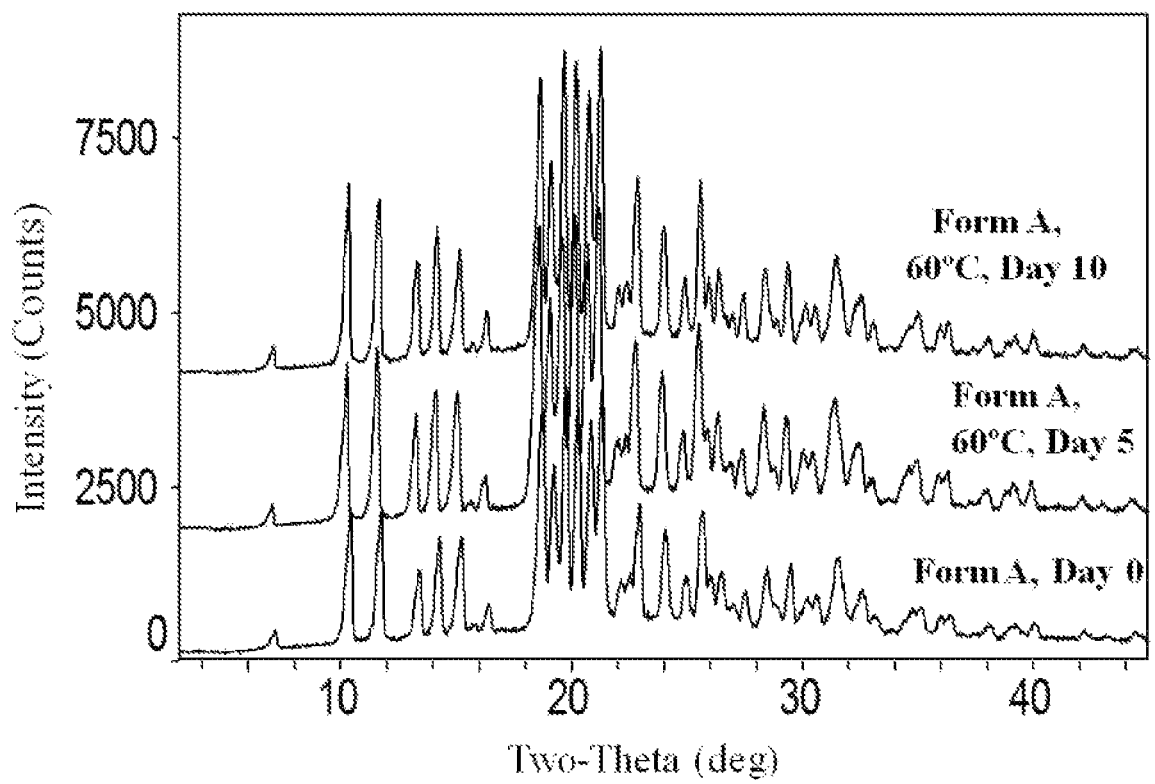
FIG. 16 shows comparison of XRPD patterns of crystal form A of the present application to study stability under high temperatures.

(2) High-temperature stability: the test sample is placed at a temperature of 60° C. for 5 days and 10 days, respectively, to test the stability of the crystal form, which are compared with XRPD pattern of the crystal form A on day 0. The results are shown in FIG. 16, indicating that the crystal form A has good high-temperature stability.

Figure 17:
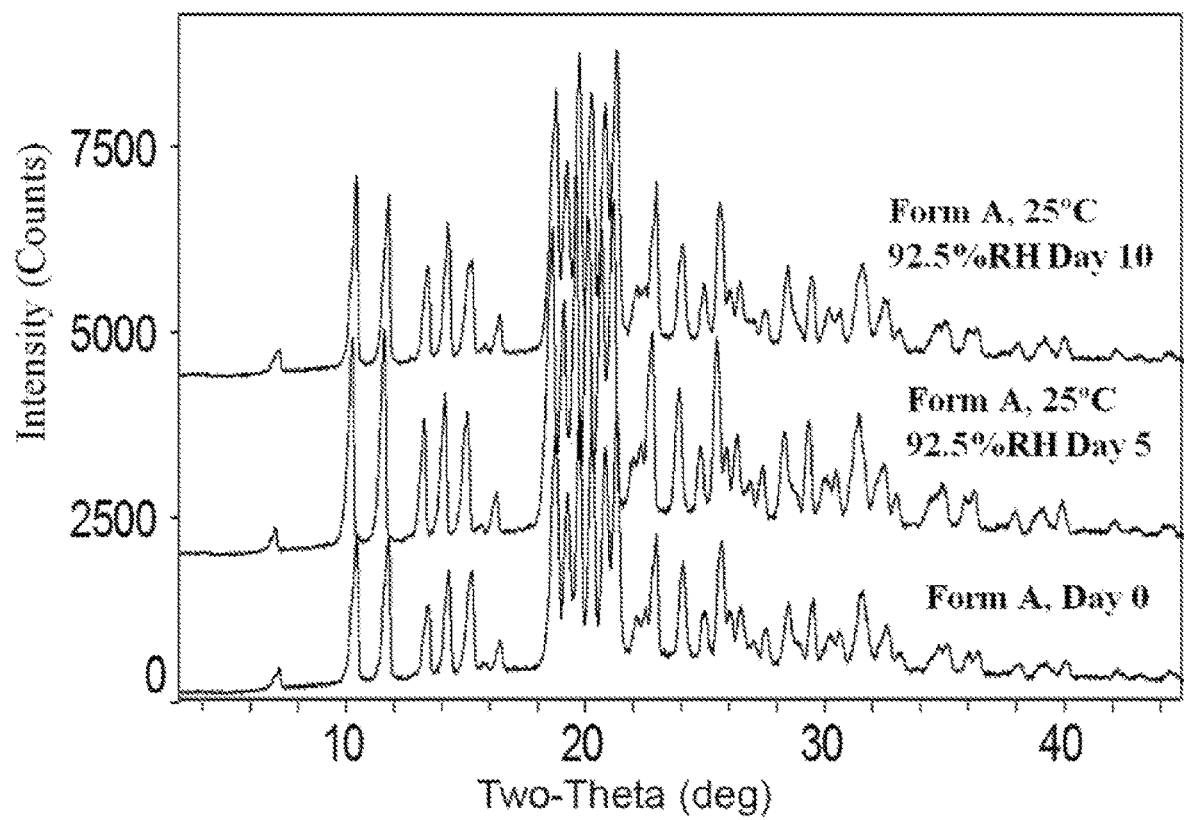
FIG. 17 shows comparison of XRPD patterns of crystal form A of the present application to study stability under high humidity 1.

(3) High-humidity stability 1: the test sample is placed in an environment having a humidity of 92.5% RH and a temperature of 25° C. for 5 days and 10 days, respectively, to test the stability of the crystal form, which are compared with XRPD pattern of the crystal form A on day 0. The results are shown in FIG. 17, indicating that the crystal form A has good high-humidity stability.

Figure 18:
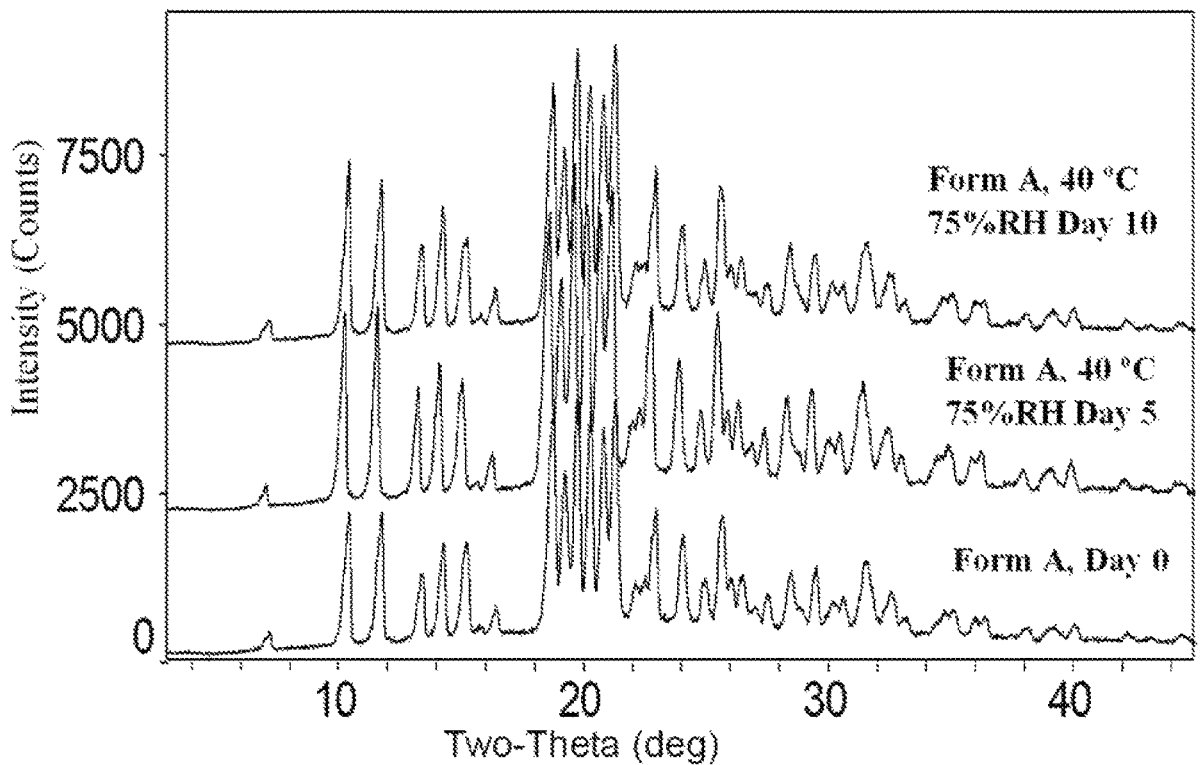
FIG. 18 shows comparison of XRPD patterns of crystal form A of the present application to study stability under high humidity 2.

(4) High-humidity stability 2: the test sample is placed in an environment having a humidity of 75% RH and a temperature of 40° C. for 5 days and 10 days, respectively, to test the stability of the crystal form, which are compared with XRPD pattern of the crystal form A on day 0. The results are shown in FIG. 18, indicating that the crystal form A has good high-humidity stability.

Experimental Example 4 Stability Study of Crystal Form I

Figure 19:
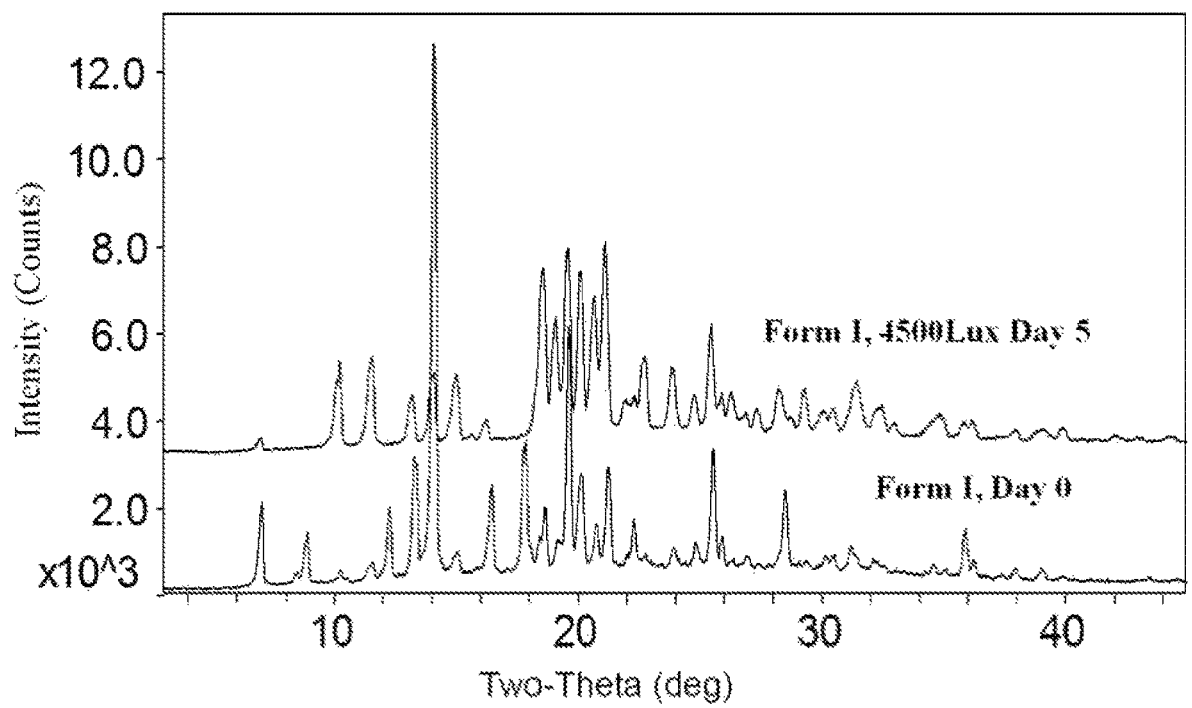
FIG. 19 shows comparison of XRPD patterns of crystal form I in Experimental Example 4 of the present application to study stability under lights.

Following tests are performed for the crystal form I prepared in Example 1:

(1) Light stability: by referring to the same method of light stability test for crystal A, the test sample is placed in an environment having a temperature of 25° C. and a light condition of 4500 Lux for 5 days to test the stability of the crystal form, which is compared with XRPD pattern of the crystal form I on day 0. The results are shown in FIG. 19, indicating that the crystal form I is unstable under lights and easily transforms into crystal form A.

Figure 20:
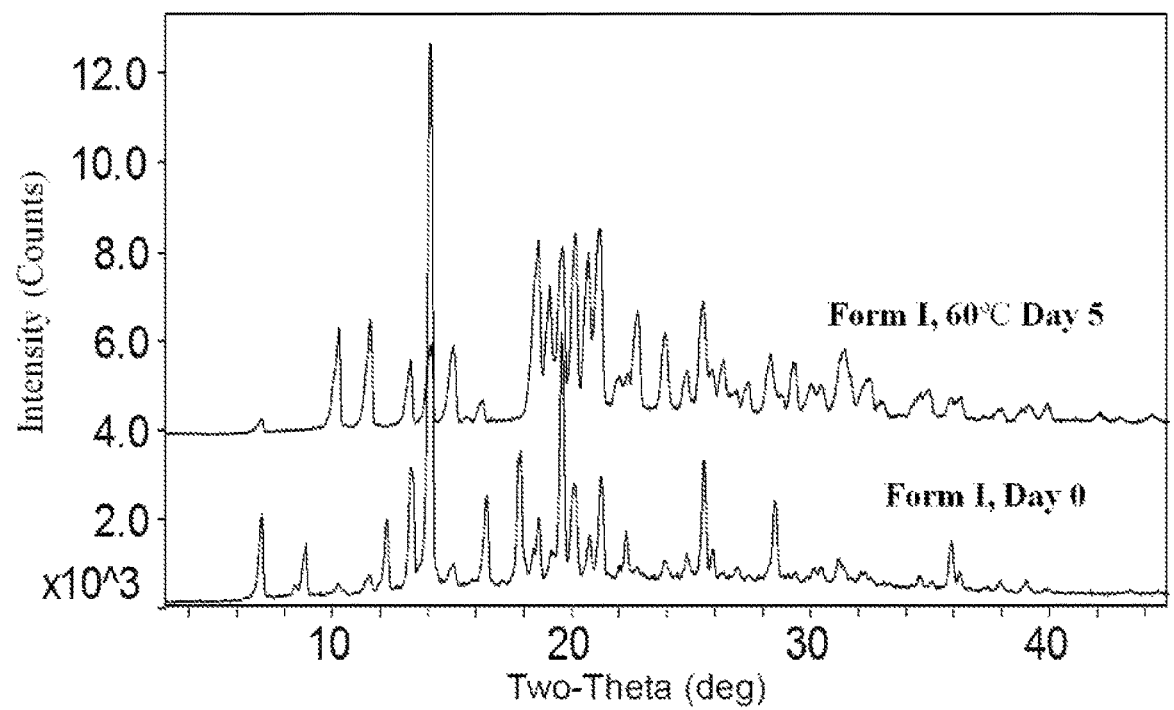
FIG. 20 shows comparison of XRPD patterns of crystal form I in Experimental Example 4 of the present application to study stability under temperatures.

(2) High-temperature stability: by referring to the same method of high-temperature stability test for crystal A, the test sample is placed at a temperature of 60° C. for 5 days to test the stability of the crystal form, which is compared with XRPD pattern of the crystal form I on day 0. The results are shown in FIG. 20, indicating that the crystal form I is unstable under high temperatures and easily transforms into crystal form A.

Figure 21:
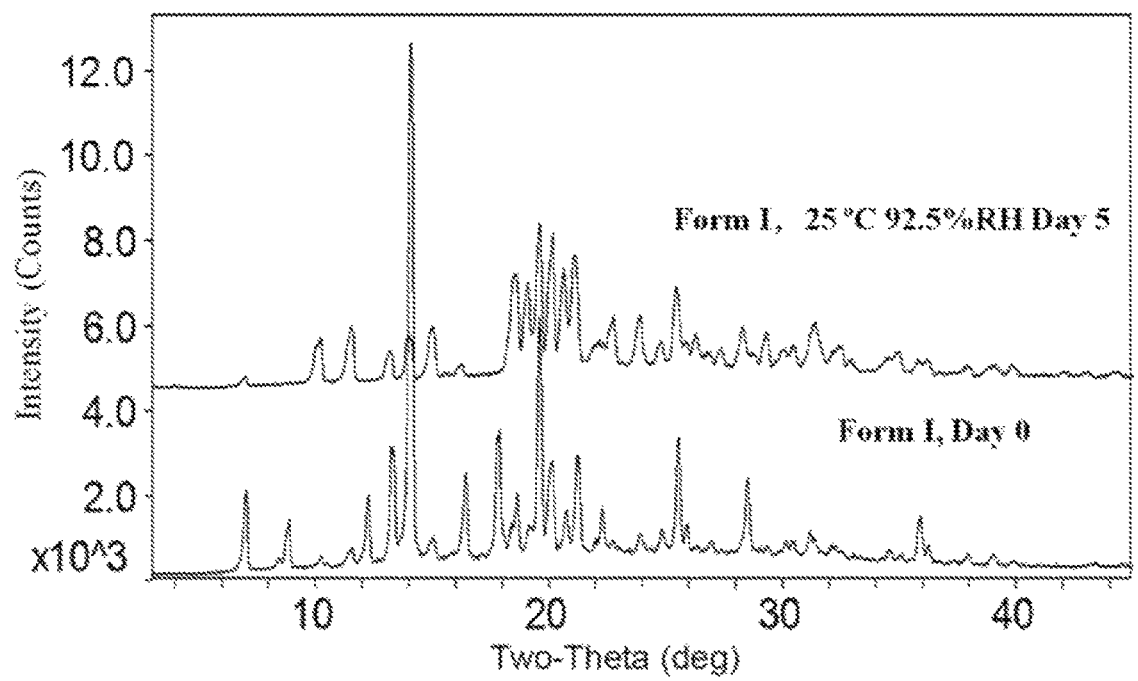
FIG. 21 shows comparison of XRPD patterns of crystal form I in Experimental Example 4 of the present application to study stability under high humidity 1.

(3) High-humidity stability 1: by referring to the same method of high-humidity stability test 1 for crystal A, the test sample is placed in an environment having a humidity of 92.5% RH and a temperature of 25° C. for 5 days to test the stability of the crystal form, which are compared with XRPD pattern of the crystal form I on day 0. The results are shown in FIG. 21, indicating that the crystal form I is unstable under high humidity and easily transforms into crystal form A.

Figure 22:
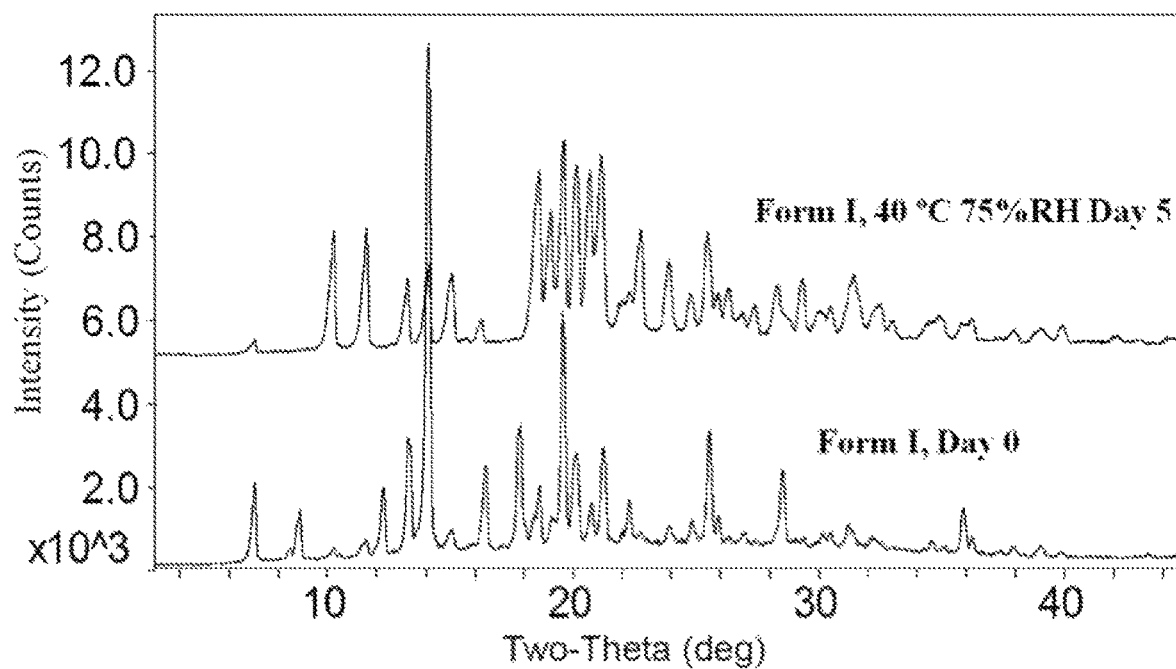
FIG. 22 shows comparison of XRPD patterns of crystal form I in Experimental Example 4 of the present application to study stability under high humidity 2.

(4) High-humidity stability 2: by referring to the same method of high-humidity stability test 2 for crystal A, the test sample is placed in an environment having a humidity of 75% RH and a temperature of 40° C. for 5 days to test the stability of the crystal form, which are compared with XRPD pattern of the crystal form I on day 0. The results are shown in FIG. 22, indicating that the crystal form I is unstable under high humidity and easily transforms into crystal form A.

In summary, the crystal form I of 2,2-bis(4-fluorophenyl)-2-phenylacetamide is poor in light stability, high-temperature stability and high-humidity stability, and has a tendency to transform to the crystal form A of 2,2-bis(4-fluorophenyl)-2-phenylacetamide of the present application. The crystal form A of 2,2-bis(4-fluorophenyl)-2-phenylacetamide provided in the present application has good light stability, high-temperature stability and high-humidity stability.

It should be noted that the terms Form A and Form I marked in the drawings of the present application represent the crystal form A and crystal form I respectively.

Apparently, the aforementioned embodiments are merely examples illustrated for clearly describing the present application, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present application.

While embodiments incorporating the principles of the present disclosure have been disclosed hereinabove, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A crystal form A of 2,2-bis(4-fluorophenyl)-2-phenylacetamide, wherein the X-ray powder diffraction thereof using Cu-Kα radiation has characteristic peaks at 2θ diffraction angles of 10.4±0.2°, 11.8±0.2°, 18.8±0.2° and 21.3±0.2°.

2. The crystal form A of claim 1, wherein the X-ray powder diffraction thereof using Cu-Kα radiation has further characteristic peaks at 2θ diffraction angles of 7.2±0.2°, and 20.8±0.2°.

3. The crystal form A of claim 2, wherein the X-ray powder diffraction thereof using Cu-Kα radiation has further characteristic peaks at 2θ diffraction angles of 15.2±0.2°, 23.0±0.2°, and 25.7±0.2°.

4. The crystal form A of claim 3, wherein the X-ray powder diffraction thereof using Cu-Kα radiation has further characteristic peaks at 2θ diffraction angles of 13.4±0.2°, 14.3±0.2°, 16.4±0.2°, 19.2±0.2°, 19.8±0.2°, 20.3±0.2°, and 24.1±0.2°.

5. The crystal form A of claim 4, wherein the X-ray powder diffraction thereof using Cu-Kα radiation has further characteristic peaks at 2θ diffraction angles of 22.1±0.2°, 22.5±0.2°, 25.0±0.2°, 26.5±0.2°, 27.5±0.2°, 28.5±0.2°, 29.5±0.2°, 31.6±0.2°, and 32.6±0.2°.

6. The crystal form A of claim 1, wherein the crystal form A has following characteristic peaks in X-ray powder diffraction pattern:

| No. of Peaks | 2θ (°) | I % |
| --- | --- | --- |
| 1 | 10.44 | 48.4 |
| 2 | 11.779 | 48.1 |
| 3 | 13.381 | 24 |
| 4 | 14.299 | 32.1 |
| 5 | 15.22 | 38.1 |
| 6 | 18.76 | 100 |
| 7 | 19.24 | 47 |
| 8 | 19.78 | 57.3 |
| 9 | 20.28 | 52 |
| 10 | 20.84 | 69.3 |
| 11 | 21.339 | 80.1 |
| 12 | 22.96 | 40.4 |
| 13 | 24.08 | 32.7 |
| 14 | 25.699 | 48.5. |

7. The crystal form A of claim 1, wherein the crystal form A has following characteristic peaks in X-ray powder diffraction pattern:

| No. of Peaks | 2-Theta | I % |
| --- | --- | --- |
| 1 | 7.163 | 6.4 |
| 2 | 10.44 | 48.4 |
| 3 | 11.779 | 48.1 |
| 4 | 13.381 | 24 |
| 5 | 14.299 | 32.1 |
| 6 | 15.22 | 38.1 |
| 7 | 16.401 | 7.4 |
| 8 | 18.76 | 100 |
| 9 | 19.24 | 47 |
| 10 | 19.78 | 57.3 |
| 11 | 20.28 | 52 |
| 12 | 20.84 | 69.3 |
| 13 | 21.339 | 80.1 |
| 14 | 22.96 | 40.4 |
| 15 | 24.08 | 32.7 |
| 16 | 24.962 | 12 |
| 17 | 25.699 | 48.5 |
| 18 | 26.5 | 11.1 |
| 19 | 27.54 | 8.4 |
| 20 | 28.46 | 25.9 |
| 21 | 29.517 | 15.8 |
| 22 | 31.58 | 36 |
| 23 | 32.599 | 18. |

Figure 4:
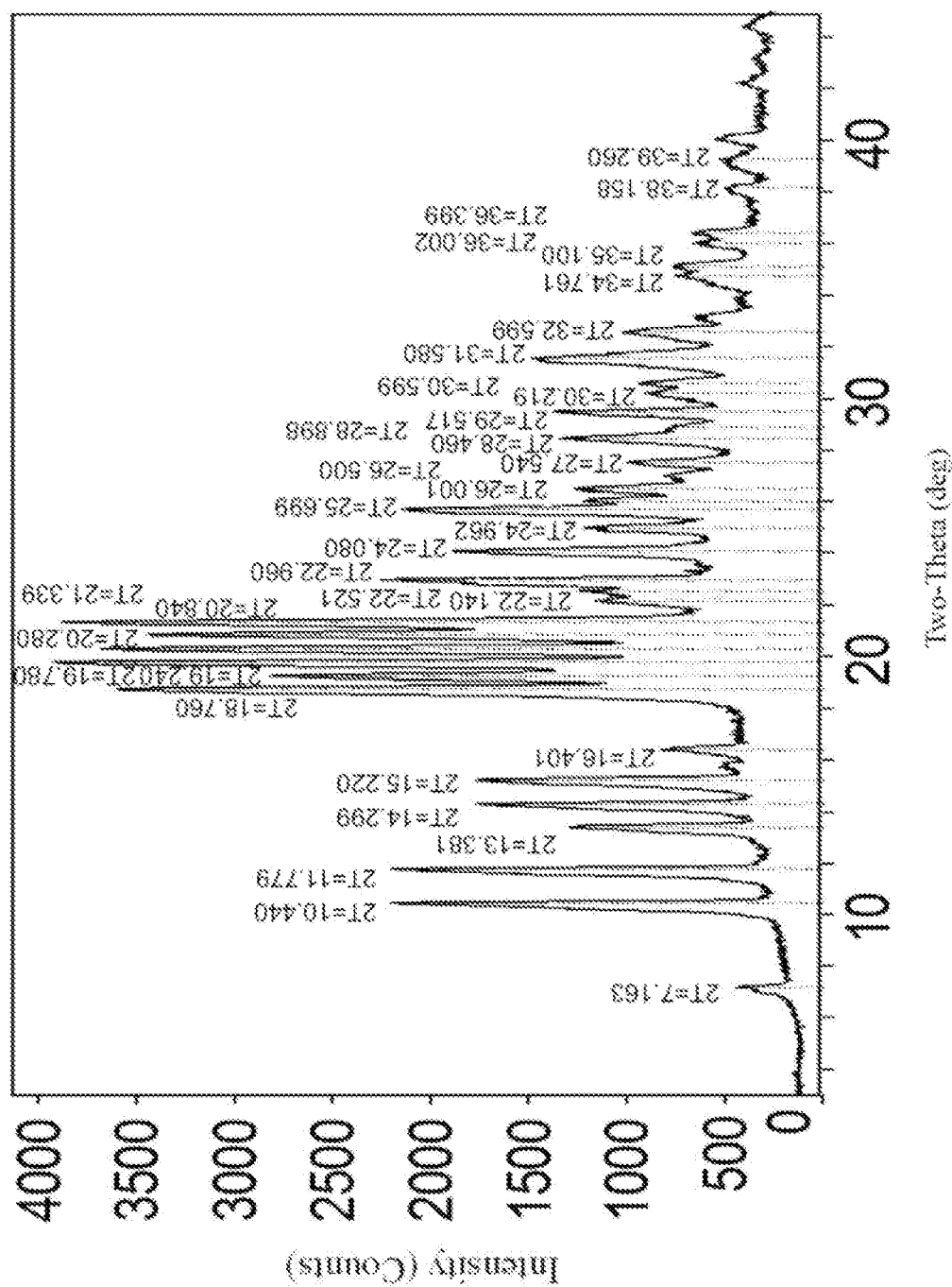
FIG. 4 shows an XRPD pattern (peak positions are marked) of crystal form A in Example 2 of the present application.

8. The crystal form A of claim 1, wherein the crystal form A has an X-ray powder refraction pattern substantially as shown in FIG. 4.

9. The crystal form A of claim 1, wherein the crystal form A has a characteristic endothermic peak in a temperature range of 177.0° C.-191.0° C. measured by differential scanning calorimetry.

10. The crystal form A of claim 1, wherein the crystal form A has a differential scanning calorimetry curve substantially as shown in FIG. 5.

11. The crystal form A of claim 1, wherein the crystal form A has a weight loss of 0.02584% before a temperature of 100° C. in its thermo gravimetric analysis curve.

12. The crystal form A of claim 1, wherein the crystal form A has a thermo gravimetric analysis curve substantially as shown in FIG. 6.

13. A method for preparing the crystal form A of claim 1, comprising the following steps of:

dissolving 2,2-bis(4-fluorophenyl)-2-phenylacetamide by adding a good solvent thereto, evaporating the solvent or cooling to give a solid, and drying the solid to obtain the crystal form A.

14. The method of claim 13, wherein said dissolving is performed by adding the good solvent at a temperature of 50° C. to 75° C., and said cooling is performed at a temperature of −18° C. to 5° C. to give a solid.

15. A method for preparing the crystal form A of claim 1, comprising the following steps of:
dissolving 2,2-bis(4-fluorophenyl)-2-phenylacetamide by adding a good solvent thereto, then adding a poor solvent to obtain a solid, and drying the solid to obtain the crystal form A.

16. The method of claim 15, wherein said dissolving is performed by adding the good solvent at a temperature of 15° C. to 35° C. and said adding a poor solvent is performed at a temperature of 15° C. to 35° C. to obtain a solid.

17. The method of claim 13, wherein the good solvent is an organic solvent selected from the group consisting of a lower alcohol, a lower ketone, a lower ester, a lower nitrile, and a lower ether.

18. The method of claim 13, wherein a ratio of 2,2-bis(4-fluorophenyl)-2-phenylacetamide to the good solvent is (10-40) mg: (0.1-5) mL.

19. The method of claim 15, wherein the poor solvent is select from n-heptane, n-hexane, absolute ethyl ether, isopropyl ether or water.

20. A pharmaceutical composition, comprising the crystal form A of claim 1 and a pharmaceutically acceptable excipient.

21. A method for preventing or treating an inflammatory process or stroke, inhibition of cell potassium channel, reduction of erythrocyte dehydration, treatment or prevention of sickle cell disease, or enhancement of the resistance to degradation of a phenyl-containing potassium channel inhibitor in a biological medium, comprising administering a pharmaceutically effective amount of the crystal form A of claim 1 or a pharmaceutical composition comprising the same.

22. The method of claim 21, wherein the inflammatory process is selected from the group consisting of multiple sclerosis, insulin-dependent diabetes mellitus, rheumatoid arthritis, peripheral neuritis, and pulmonary hypertension.

23. The method of claim 21, wherein the medicament is administered orally, parenterally, intradermally, intrathecally, intramuscularly, subcutaneously, vaginally, as a buccal, sublingually, rectally, as a topical, inhalation, intranasal, or transdermally.

24. The method of claim 17, wherein the lower alcohol is selected from the group consisting of methanol, ethanol, isopropanol and n-butanol, the lower ketone is acetone, the lower ester is ethyl acetate, the lower ether is tetrahydrofuran or dioxane, and the lower nitrile is acetonitrile.

* * * * *